US00PP15458P2

(12) United States Plant Patent
van Rijn

(10) Patent No.: US PP15,458 P2
(45) Date of Patent: Dec. 28, 2004

(54) *ANTHURIUM* PLANT NAMED 'RIJN200121'

(50) Latin Name: *Anthurium andreanum*
Varietal Denomination: Rijn200121

(75) Inventor: Leonardus W. B. M. van Rijn, Schipluiden (NL)

(73) Assignee: Rijnplant B.V., Schipluiden (NL)

( * ) Notice: Subject to any disclaimer, the term of this patent is extended or adjusted under 35 U.S.C. 154(b) by 0 days.

(21) Appl. No.: 10/766,771

(22) Filed: Jan. 28, 2004

(51) Int. Cl.[7] ..... A01H 5/00

(52) U.S. Cl. ..... Plt./365

(58) Field of Search ..... Plt./365, 366

*Primary Examiner*—Anne Marie Grunberg
*Assistant Examiner*—June Hwu
(74) *Attorney, Agent, or Firm*—C. A. Whealy

(57) ABSTRACT

A new and distinct cultivar of *Anthurium* plant named 'Rijn200121', characterized by its upright and outwardly spreading plant habit; freely clumping growth habit; durable dark green leaves; white and green-colored spathes with light yellow-colored spadices that are positioned above and beyond the foliage on strong and erect scapes; freely flowering habit; and good inflorescence longevity.

1 Drawing Sheet

Botanical classification/cultivar designation: *Anthurium andreanum* cultivar Rijn200121.

BACKGROUND OF THE INVENTION

The present invention relates to a new and distinct cultivar of *Anthurium* plant, botanically known as *Anthurium andreanum,* and hereinafter referred to by the name 'Rijn200121'.

The new *Anthurium* is a product of a planned breeding program conducted by the Inventor in Schipluiden, The Netherlands. The objective of the program is to create and develop new compact, freely clumping and freely flowering *Anthurium* cultivars with strong roots, dark green leaves, attractive spathe color, and good inflorescence longevity.

The new *Anthurium* originated from a cross by the Inventor on Jun. 22, 1999 of a proprietary selection of *Anthurium andreanum* identified as code number 9715, not patented, as the female, or seed, parent with a proprietary selection of *Anthurium andreanum* identified as code number 9713, not patented, as the male, or pollen, parent. The cultivar Rijn200121 was discovered and selected by the Inventor as a flowering plant within the progeny of the stated cross in a controlled environment in Schipluiden, The Netherlands on Apr. 24, 2001.

Asexual reproduction of the new cultivar by meristem culture in a laboratory in Belgium since April, 2001, has shown that the unique features of this new *Anthurium* plant are stable and reproduced true to type in successive generations of asexual propagation.

BRIEF SUMMARY OF THE INVENTION

The new *Anthurium* has not been observed under all possible environmental conditions. The phenotype may vary somewhat with variations in environment such as temperature and light intensity, without, however, any variance in genotype.

The following traits have been repeatedly observed and are determined to be the unique characteristics of the cultivar Rijn200121. These characteristics in combination distinguish 'Rijn200121' as a new and distinct cultivar:

1. Upright and outwardly spreading plant habit.
2. Freely clumping growth habit.
3. Durable dark green-colored leaves.
4. White and green-colored spathes with light yellow-colored spadices that are positioned above and beyond the foliage on strong and erect scapes.
5. Freely flowering habit.
6. Good inflorescence longevity.

Plants of the new *Anthurium* can be compared to plants of the female parent, the proprietary selection identified as code number 9715. In side-by-side comparisons conducted in Schipluiden, The Netherlands, plants of the new *Anthurium* differed from plants of the selection 9715 in the following characteristics:

1. Plants of the new *Anthurium* were more compact than plants of the selection 9715.
2. Plants of the new *Anthurium* had flatter spathes than plants of the selection 9715.
3. Plants of the new *Anthurium* and the selection 9715 differed in spathe coloration as plants of the selection 9715 had white and red-colored spathes.

Plants of the new *Anthurium* can be compared to plants of the male parent, the selection 9713. In side-by-side comparisons conducted in Schipluiden, The Netherlands, plants of the new *Anthurium* differed from plants of the selection 9713 primarily in spathe coloration as plants of the selection 9713 had pink and green-colored spathes.

Plants of the new *Anthurium* can be compared to plants of the cultivar Fresh Love, disclosed in U.S. Plant Pat. No. 13,349. In side-by-side comparisons conducted in Schipluiden, The Netherlands, plants of the new *Anthurium* differed from plants of the cultivar Fresh Love in the following characteristics:

1. Plants of the new *Anthurium* were more compact than plants of the cultivar Fresh Love.
2. Plants of the new *Anthurium* had smaller and darker green-colored leaves than plants of the cultivar Fresh Love.
3. Plants of the new *Anthurium* had flatter spathes than plants of the cultivar Fresh Love.

BRIEF DESCRIPTION OF THE PHOTOGRAPHS

The accompanying colored photographs illustrate the overall appearance of the new *Anthurium,* showing the colors as true as it is reasonably possible to obtain in colored reproductions of this type. Colors in the photographs may differ slightly from the color values cited in the detailed botanical description which accurately describe the colors of the new *Anthurium.*

The photograph at the top of the sheet comprises a side perspective view of a typical flowering plant of the cultivar Rijn200121.

The photograph at the bottom of the sheet comprises a close-up view of typical inflorescences of 'Rijn200121'.

DETAILED BOTANICAL DESCRIPTION

In the following description, color references are made to The Royal Horticultural Society Colour Chart, 2001 Edition, except where general terms of ordinary dictionary significance are used. The aforementioned photographs and the following observations and measurements describe seven-month old plants grown in 14-cm containers in Schipluiden, The Netherlands, in a glass-covered greenhouse with average day temperatures of 23° C., average night temperatures of 21° C. and light levels about 6 kilolux.

Botanical classification: *Anthurium andreanum* cultivar Rijn200121.

Parentage:

*Female parent.*—Proprietary selection of *Anthurium andreanum* identified as code number 9715, not patented.

*Male parent.*—Proprietary selection of *Anthurium andreanum* identified as code number 9713, not patented.

Propagation:

*Method.*—By meristem culture.

*Time to initiate roots on a meristem-cultured plant.*—About four weeks at 20 to 24° C.

*Time to develop roots on a meristem-cultured plant.*—About nine months at 20 to 24° C.

*Root description.*—Thick, fleshy, dark pink to cream-colored; lateral roots, thick and abundant.

Plant description:

*Plant shape.*—Upright and outwardly spreading plant habit, inverted triangle, symmetrical.

*Growth habit.*—Freely clumping, bushy and dense growth habit; about nine clumps per plant; moderately vigorous.

*Plant height, from soil level to top of leaf plane.*—About 33 cm.

*Plant height, from soil level to top of inflorescences.*—About 36 cm.

*Plant diameter or spread.*—About 41 cm.

*Foliage description.*—Arrangement: Alternate; simple. Length: About 11.4 cm. Width: About 9.3 cm. Shape: Cordate. Apex: Apiculate. Base: Cordate. Margin: Entire. Texture, upper and lower surfaces: Leathery; glabrous, smooth; durable. Venation pattern: Pinnate. Color: Developing leaves, upper surface: Slightly darker than 146A. Developing leaves, lower surface: 146A. Fully developed leaves, upper surface: Between 139A and 147A. Fully developed leaves, lower surface: Between 143A and 146A. Venation, upper surface: 143B. Venation, lower surface: 144A. Petiole: Length: About 18.9 cm. Diameter, just below geniculum: About 3.5 mm. Diameter, at plant base: About 5.5 mm. Texture: Smooth, glabrous. Color: 143A. Geniculum length: About 1.3 cm. Geniculum diameter: About 4 mm. Geniculum color: 143A slightly tinted with 177B to 177C. Wing length: About 3.9 cm. Wing diameter: About 6 mm. Wing color: 143A to 144A to 144B.

Inflorescence description:

*Inflorescence arrangement.*—Spathes with spadices held above and beyond the foliage. Flowering structures arise from leaf axils. Freely and continuous flowering during the autumn in Schipluiden, The Netherlands. Typically about six inflorescences per plant. Inflorescences not fragrant.

*Inflorescence longevity.*—Inflorescences last about two months under winter conditions and about three months under summer conditions; inflorescences persistent.

*Spathe.*—Length: About 5.9 cm. Width: About 7.6 cm. Shape: Broadly cordate with reniform tendencies. Apex: Abruptly acute; reflexed. Base: Obtuse to cordate. Margin: Entire. Texture, upper and lower surfaces: Leathery; glabrous, smooth. Aspect: Mostly flat. Color: When developing and fully developed, front surface: 159D; towards the margins, 144B to 144C; color becoming closer to 144A with development. When developing and fully developed, rear surface: 157C; towards the margins, 144C.

*Spadix.*—Length: About 4.8 cm. Width: About 8 mm. Shape: Columnar, tapering towards the apex; apex, obtuse. Cross section: Rounded. Aspect: About 10° from vertical. Color: Immature: 23D; towards the apex, 160B. Mature: 19D; towards the apex, 22C.

*Flowers.*—Quantity per spadix: Numerous, about 325. Shape: Rounded. Height: Less than 0.5 mm. Diameter: About 0.8 mm.

*Reproductive organs.*—Androecium: Anther color: 11D. Amount of pollen: Moderate. Pollen color: 11C to 11D. Gynoecium: Stigma shape: Ovoid. Stigma color: 157A. Ovary color: 157A.

*Scape.*—Length: About 22.1 cm. Diameter: About 4 mm. Strength: Strong. Aspect: Erect to slightly outwardly slanted to about 10° from vertical. Color: 144A.

*Seed and fruit.*—Seed and fruit development has not been observed on plants of the new *Anthurium.*

Disease/pest resistance: Under commercial production conditions, plants of the new *Anthurium* have not been observed to be resistant to pathogens or pests common to *Anthurium.*

Temperature tolerance: Plants of the new *Anthurium* have been observed to tolerate temperatures from about 14 to 36° C.

It is claimed:

1. A new and distinct cultivar of *Anthurium* plant named 'Rijn200121', as illustrated and described.

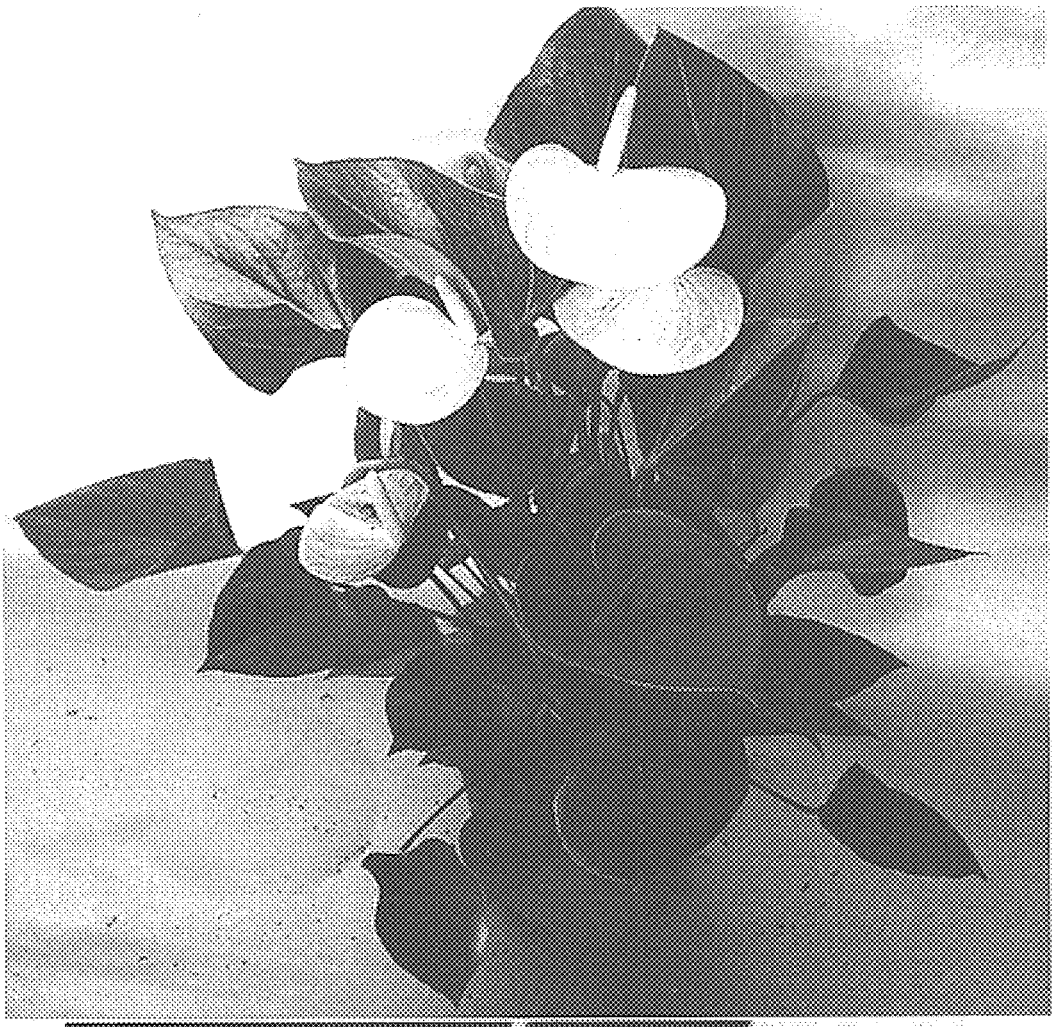
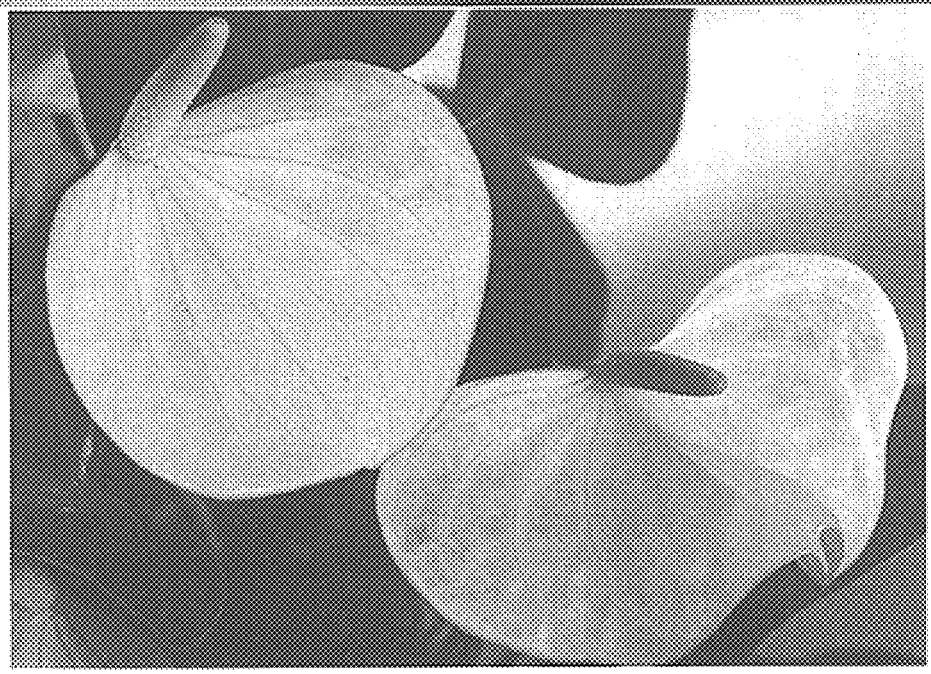

* * * * *